US011350957B2

(12) United States Patent
Blus et al.

(10) Patent No.: US 11,350,957 B2
(45) Date of Patent: Jun. 7, 2022

(54) LAPAROSCOPIC FORCEPS ASSEMBLY FOR GRIPPING AND DISSECTION

(71) Applicant: GYRUS ACMI, INC., Southborough, MA (US)

(72) Inventors: Theodore C. Blus, Arden Hills, MN (US); Zane R Ward, Prior Lake, MN (US); Jeffrey J. Nelson, Plymouth, MN (US); Riyad Moe, Madison, WI (US)

(73) Assignee: Gyms Acmi, Inc., Westborough, MA (US)

( * ) Notice: Subject to any disclaimer, the term of this patent is extended or adjusted under 35 U.S.C. 154(b) by 217 days.

(21) Appl. No.: 16/365,854

(22) Filed: Mar. 27, 2019

(65) Prior Publication Data

US 2020/0305903 A1 Oct. 1, 2020

(51) Int. Cl.
*A61B 17/29* (2006.01)
*A61B 17/00* (2006.01)

(52) U.S. Cl.
CPC .... *A61B 17/29* (2013.01); *A61B 2017/00424* (2013.01); *A61B 2017/2932* (2013.01)

(58) Field of Classification Search
CPC . A61B 18/1442; A61B 18/1445; A61B 10/06; A61B 2017/2932–2944; A61B 2017/00424; A61B 2017/2922; A61B 2017/2919; A61B 2017/00353; A61B 2017/320044; A61B 17/320016; A61B 17/28; A61B 17/2841; A61B 17/29; A61B 17/32; A61B 2017/2912–2923; A61B 2017/2925; A61B 17/00424; A61B 17/2909; A61B 17/2932
See application file for complete search history.

(56) References Cited

U.S. PATENT DOCUMENTS

| 4,887,612 A | 12/1989 | Esser et al. |
| 5,286,255 A | 2/1994 | Weber |
| 5,354,313 A | 10/1994 | Boebel |
| 5,413,583 A | 5/1995 | Wohlers |
| 5,445,638 A | 8/1995 | Rydell et al. |
| 5,480,409 A | 1/1996 | Riza |

(Continued)

FOREIGN PATENT DOCUMENTS

| DE | 19751731 A1 | 5/1999 |
| EP | 0538984 A2 | 4/1993 |

(Continued)

OTHER PUBLICATIONS

Potentially Related Patent Application, U.S. Appl. No. 15/839,218, filed Dec. 12, 2017.

(Continued)

*Primary Examiner* — Robert A Lynch
(74) *Attorney, Agent, or Firm* — Schwegman Lundberg & Woessner, P.A.

(57) ABSTRACT

A surgical device can include a first jaw, a second jaw opposing the first jaw, a clamp lever in communication with the first jaw and the second jaw and operable to move the first jaw, the second jaw, or both from a jaw nominal position to a jaw clamped position when an external force is imparted upon the clamp lever in a first direction, and a stop bias member that stops movement of the clamp lever when the external force is removed so that the first jaw and the second jaw are in the jaw nominal position at rest.

18 Claims, 6 Drawing Sheets

(56) References Cited

U.S. PATENT DOCUMENTS

| | | | |
|---|---|---|---|
| 5,562,699 A | 10/1996 | Heimberger | |
| 5,626,608 A * | 5/1997 | Cuny | A61B 17/2909 |
| | | | 600/131 |
| 5,653,721 A | 8/1997 | Knodel | |
| 5,683,412 A | 11/1997 | Scarfone | |
| 5,735,849 A | 4/1998 | Baden et al. | |
| 5,776,130 A | 7/1998 | Buysse et al. | |
| 5,944,723 A | 8/1999 | Colleran et al. | |
| 5,947,984 A | 9/1999 | Whipple | |
| 5,984,938 A | 11/1999 | Yoon | |
| 6,039,733 A | 3/2000 | Buysse et al. | |
| 6,113,596 A | 9/2000 | Hooven et al. | |
| 6,190,386 B1 | 2/2001 | Rydell | |
| 6,270,497 B1 | 8/2001 | Sekino et al. | |
| 6,458,130 B1 | 10/2002 | Frazier et al. | |
| 6,585,735 B1 | 7/2003 | Frazler | |
| 6,679,882 B1 | 1/2004 | Kornerup | |
| 6,752,823 B2 | 6/2004 | Prestel | |
| 7,083,618 B2 | 8/2006 | Couture et al. | |
| 7,101,372 B2 | 9/2006 | Dycus et al. | |
| 7,118,587 B2 | 10/2006 | Dycus et al. | |
| 7,384,420 B2 | 6/2008 | Dycus et al. | |
| 7,604,634 B2 | 10/2009 | Hooven | |
| 7,628,791 B2 | 12/2009 | Garrison et al. | |
| 7,766,910 B2 | 8/2010 | Hixson et al. | |
| 8,298,232 B2 | 10/2012 | Unger | |
| 8,475,453 B2 | 7/2013 | Marczyk et al. | |
| 8,647,341 B2 | 2/2014 | Dycus et al. | |
| 8,672,935 B2 | 3/2014 | Okada et al. | |
| 8,734,443 B2 | 5/2014 | Hixson et al. | |
| 9,113,903 B2 | 8/2015 | Unger | |
| 9,216,030 B2 | 12/2015 | Fan et al. | |
| 9,579,117 B2 | 2/2017 | Kappus et al. | |
| 9,788,848 B2 | 10/2017 | Ward et al. | |
| 2006/0235438 A1 | 10/2006 | Huitema et al. | |
| 2012/0157995 A1* | 6/2012 | Deville | A61B 18/1445 |
| | | | 606/46 |
| 2013/0131666 A1 | 5/2013 | Atwell et al. | |
| 2014/0135805 A1 | 5/2014 | Windgassen et al. | |
| 2017/0354456 A1 | 12/2017 | Fiksen et al. | |
| 2018/0296213 A1 | 10/2018 | Strobl | |
| 2019/0175256 A1* | 6/2019 | Butler | A61B 18/1445 |
| 2020/0289192 A1* | 9/2020 | Sawyer | A61B 18/1482 |

FOREIGN PATENT DOCUMENTS

| | | | | |
|---|---|---|---|---|
| WO | WO-2009046490 A1 * | 4/2009 | | A61B 17/29 |
| WO | WO-2010088595 A1 | 8/2010 | | |
| WO | WO-2010098871 A2 * | 9/2010 | | A61B 1/00087 |

OTHER PUBLICATIONS

"European Application Serial No. 20164748.4, Extended European Search Report dated Aug. 10, 2020", 7 pgs.

"European Application Serial No. 20164748.4, Response filed Mar. 24, 2021 to Extended European Search Report dated Aug. 10, 2020", 61 pgs.

* cited by examiner

LAPAROSCOPIC FORCEPS ASSEMBLY FOR GRIPPING AND DISSECTION

FIELD

The disclosure relates to forceps with a nominal position where jaws of the forceps are movable to a clamped position and then into a spread position where a distance between the jaws is greater than a distance between the jaws in the nominal position.

BACKGROUND

Generally forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. Laparoscopic forceps may have resilient jaws or rigid body jaws for gripping and treating tissues. Movement of a trigger may close the jaws to create a gripping force. The resilient jaws may be closed by a tube overrunning the jaws or the jaws being retracted into a tube so that the tube is closed. The rigid body jaws may be closed by a driver moving that is connected to the jaws and as the driver moves the jaws are biased into a closed position. Examples of some forceps with resilient jaws closed by a camming action may be found in U.S. Pat. Nos. 4,887,612; 5,286,255; 5,354,313; 5,735,849; 5,445,638; 5,984,938; 6,190,386; 6,113,596; 6,458,130; 6,679,882; 7,118,587; 9,216,030; and 9,788,848 all of which are incorporated by reference herein in their entirety for all purposes.

It would be attractive for the forceps to be usable for blunt dissection. What is needed is a device that assists in driving the jaws apart so that a distance between the jaws is increased relative to a jaw nominal position or a default position. What is needed is a device that allows the user to spread the jaws apart when the jaws are in the jaw nominal position. It would be attractive to have a device that spreads the jaws with sufficient force so that the jaws can be used for dissection. What is needed is a device that returns the jaws back to a jaw nominal position once a force is released.

SUMMARY

The disclosure meets one or more of the needs by providing: A surgical device comprising: (a) a first jaw; (b) a second jaw opposing the first jaw, the first jaw, the second jaw, or both being movable relative to one another between a jaw nominal position and a jaw clamped position; (c) a clamp lever in communication with the first jaw and the second jaw, the clamp lever moving the first jaw, the second jaw, or both from the jaw nominal position to the jaw clamped position when an external force is imparted upon the clamp lever in a first direction; and (d) a stop member that stops movement of the clamp lever when the external force is removed so that the first jaw and the second jaw are in the jaw nominal position at rest; wherein the first jaw and the second jaw are movable from the jaw nominal position to a jaw spread position when the clamp lever is moved in a second direction that opposes the first direction by an external force deforming the stop bias member so that a distance between the first jaw and the second jaw is larger in the jaw spread position than in the jaw nominal position.

The teachings herein provide forceps usable for blunt dissection. The teachings herein provide a device that assists in biasing the jaws apart so that a distance between the jaws is increased relative to a jaw nominal position or a default position. The teachings herein provide a device that allows the user to spread the jaws apart when the jaws are in the jaw nominal position. The teachings herein provide a device that spreads the jaws with sufficient force so that the jaws can be used for dissection. The teachings herein provide a device that returns the jaws back to a jaw nominal position once a force is released.

DETAILED DESCRIPTION

Figure 1A:
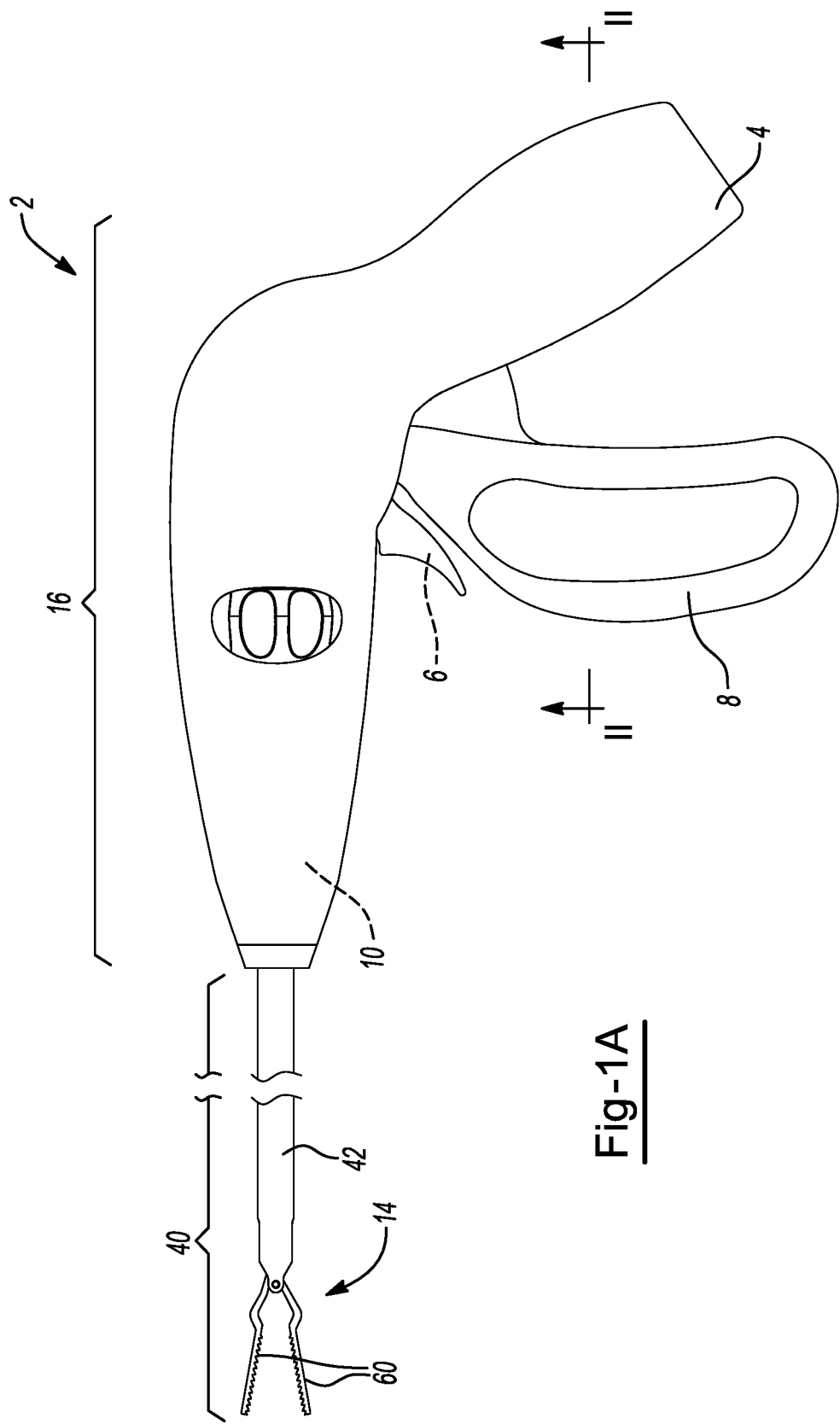
FIG. 1A illustrates a side view of laparoscopic forceps with resilient jaws.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a surgical device. The surgical device functions to grip an anatomical feature (e.g., a vein, artery, tissue, tumor, cyst, skin, muscle, a tendon, gland, tonsils, appendix, gall bladder); cut an anatomical feature, cauterize anatomical feature, or a combination thereof. The surgical device may assist in performing minimally invasive surgery. The surgical device may be an electrosurgical device. The surgical device may include one or more blades, one or more forceps, or both. Preferably, the surgical device includes an elongated stylet with forceps at an end and a reciprocating blade.

The forceps may function to grip an object. Preferably, the forceps may be used during surgery to grip a feature of interest including: a part of a body, an anatomical feature, tissue, veins, arteries, or a combination thereof. The forceps may function to be used in surgery, for example laparoscopic surgery. The forceps may be used with or without power. Current may be passed through the forceps so that the forceps are used for electrosurgery. For example, a therapy current may be passed from one jaw to a second jaw when tissue is located within the jaw and the therapy current may coagulate blood, cauterize, cut, or a combination thereof (e.g., bipolar electrosurgery). In another example, a therapy current may be passed from one or more of the jaws to a remote electrode (e.g., a return pad) (e.g., for monopolar electrosurgery). The forceps may generally include one or more working assemblies and sufficient controls to work the one or more assemblies (e.g., actuators, jaws). The forceps may be comprised of parts needed to perform the recited functions and may include generally, a stylet (e.g., a tubular member, a hollow tube, or an assembly of tubes); a hand piece; one or more operable mechanisms (e.g., actuators, bias members, triggers) used to actuate the stylet, blade, or jaws; or a combination thereof. The forceps may include two or more jaws that are movable directly towards and away from each other in a single plane. The jaws may rotate about a rotational axis so that the jaws rotate towards and away from each other along an arc. The jaws may rotate about a hinge that located at a distal end of the stylet. The jaws may have a rigid body. The jaws may rotate about a pivot. The jaws may be a rigid body that rotates about a pivot. Both jaws may be actuated by a jaw arm that is connected to each of the jaws and actuates both jaws. An axis of the jaws may remain substantially planar at all times (i.e., an end of the jaws may remain generally within a plane at all times). A tip may of the jaws may have an arcuate movement so that the forceps create a jaw clamped position. The handpiece may be an assembly of parts or structures capable of forming a handpiece structure with a cavity inside of a housing.

The handpiece may function to form an enclosing structure for the forceps, a gripping portion for the user, a main portion for manipulating the forceps, or a combination thereof. The handpiece may be any device that houses the working assemblies and parts of the forceps. The handpiece may be comprised of or include one or more housing structures. Preferably, the handpiece is or includes two or more housing structures that house a plurality of moving parts of the surgical device. The handpiece may be any structure that is gripped by a user. The handpiece may be any structure that combines one or more of the components discussed herein so that the surgical device is formed and the forceps may be actuated. The handpiece may assist in performing laparoscopic surgery. The handpiece may be ergonomically shaped. The ergonomic shape of the handpiece may be any shape so that the forceps may be used ambidextrously. The ergonomic shape of the handpiece may be any shape such that all the controls can be accessed by a single hand gripping the handpiece. The handpiece may be a generally static piece that the occupant grips and manipulates to perform one or more surgical functions or procedures. The handpiece may house all or apportion of a fixed handle, trigger, clamp lever, rounding member, actuator, return bias member, stop bias member, movement actuator, stylet, outer tube, inner tube, or a combination thereof. The handpiece may be comprised of one or more housings.

The housing may be one or more devices or pieces that form the handpiece. The housing may be an outer structure that forms an external portion of a handpiece. The housing may be any devices that may affix certain pieces into position. The housing may form a cavity to house working assemblies of the forceps, surgical device, or both. The housing may be one or more housings and preferably two or more housings. The two housings may join together to form a single housing structure. The housings may be any device that includes a recess for receiving one or more components of the forceps. The housings may be a static piece that a user grips and other portions of the surgical device may move relative to the housings. The housing structures may house all or a portion of one or more operable mechanisms (e.g., a trigger, clamp lever, actuator, return bias member, stop bias member, movement actuator, stylet, outer tube, inner tube, or a combination thereof). All or a portion of the housings may combine together to form a fixed handle.

The fixed handle may function to support the device so that the user (e.g., a surgeon) may grip the fixed handle to perform a surgery. The fixed handle may function to assist a user in creating movement of one or more adjacent parts (e.g., a trigger or clamp lever). The fixed handle may connect the surgical device to a power source. The fixed handle may extend downward from a main portion of the surgical device. The fixed handle may extend at an angle relative to the stylet. The fixed handle may include one or more locks. The one or more locks may lock the trigger, clamp lever, or both in a position relative to the fixed handle (e.g., so that the blade, forceps, stylet, or a combination thereof may be locked in a position (e.g., a closed or clamped position)). The fixed handle may be hollow. The fixed handle may be formed from part of the housing. The fixed handle may be static so that upon an application of force to a trigger, a clamp lever, or both rotational movement towards or away from the fixed handle may be imparted.

The trigger may function to actuate one or more blades. The trigger may have a portion located within the housing and a portion that extends out of the housing. The trigger may rotate in a rotational movement (e.g., an arc) towards and away from the fixed handle. The trigger may be movable into a trigger extended position where the trigger is moved to extend a blade. The trigger in a trigger extended position where the trigger is moved towards the fixed handle and the blade is moved axially toward a distal end of the stylet. The trigger may be located proximate to, in front of alongside of, extend in front of, or a combination there of a clamp lever.

The clamp lever may function to actuate the forceps. The clamp lever may move a jaw arm that moves the forceps. The clamp lever may axially move the forceps distally, proximally, or both relative to the stylet, the surgical device, or both. The clamp lever may move the forceps into the stylet, out of the stylet, or both. The clamp lever may move the forceps from a jaw nominal position to a jaw clamped position, a jaw spread position, or both. The clamp lever may be at rest at a jaw nominal position (e.g., no force may be acting upon the clamp lever). The clamp lever may have one or more forces acting upon the clamp lever or a component of the clamp lever (e.g., a movement actuator (e.g., a portion of an operable mechanism, a four-bar mechanism)) but the forces may be at steady state where the clamp lever is retained in a non-movement state. For example, the return bias member and the stop bias member may contact the movement actuator and hold the movement actuator and the clamp lever in the clamp lever nominal position. The clamp lever may rest at a zero-net force or no net force position. For example, the force of the return bias member and the stop bias member may offset each other to form a zero bias. The clamp lever nominal position may function to be a position where the clamp lever stops when forces external to the surgical device are removed. Each of the components of the surgical device may have a nominal position. The nominal position of the device may be when clamp lever is free of any external forces and thus are at rest. If a discussion herein relates to a component then that component has a nominal position (e.g., clamp lever nominal position). The clamp lever nominal position may be a position of the clamp lever where the clamp lever is located between a clamp lever clamped position and a clamp lever spread position. The clamp lever may be locked in the clamped position or closed position. The force of the return bias member and the force of the stop bias member may offset each other so that the clamp lever, the movement actuator, or both may be retained in a rest position (e.g., a jaw nominal position or a clamp lever nominal position). The return bias member and the stop bias member may each include a bias on the movement actuator, the clamp lever, or both. The clamp lever when moved towards the fixed handle may act upon the return bias member so that the return bias member is moved distally, compressed, deflected, loaded, or a combination thereof. The clamp lever may rotate about a pivot, move a four-bar mechanism, or both. The clamp lever may be connected to an operable mechanism or four bar mechanism as taught herein including the teachings found in U.S. Ser. No. 15/839,218, filed on Dec. 12, 2017 (1663.114US1), the teachings of which are expressly incorporated herein for all purposes regarding the operable mechanism and the four bar mechanism.

The operable mechanism may function to move the jaws upon movement of the clamp lever. The operable mechanism may include one or more links or bars. The operable mechanism may be an actuator, a four-bar mechanism, or both. The operable mechanism may include one or more movement actuators, one or more housings, one or more couplers, clamp lever, or a combination thereof. The operable mechanism may be a direct connection between the clamp lever and the jaw arms. The operable mechanism may have a movement actuator that is located between the clamp lever and the jaw arms. The clamp lever may move a movement actuator and the movement actuator may move the jaw arms. The clamp lever may be directly connected to a coupler. The coupler may be located between the movement actuator and clamp lever. The coupler may move an end of a movement actuator so that the jaw arms are axially moved. The coupler, clamp lever, movement actuator, or a combination thereof may each move about a rotational axis. The clamp lever, the movement actuator, or both may be connected to the housing by one or more grounding members. The coupler may float between the clamp lever and the movement actuator.

The operable mechanism may have a vertical nominal axis, a horizontal nominal axis, or both. The vertical nominal axis may extend perpendicular to a horizontal nominal axis. The vertical nominal axis may be a longitudinal axis of the movement actuator, clamp lever, coupler, or a combination thereof when the movement actuator, jaws, clamp lever, coupler, or a combination thereof are in the nominal position (e.g., jaw nominal position). The movement actuator, coupler, clamp lever, or a combination thereof may move relative to the vertical nominal axis to open the jaws, clamp the jaws, spread the jaws, or a combination thereof. The movement actuator, coupler, clamp lever, or a combination thereof may move from the vertical nominal axis to a clamped axis, a spread axis, or both. The movement actuator, coupler, clamp lever, or a combination thereof may rotate relative to each other so that an angle between each of the members varies when the jaws are moved from the jaw nominal position to a jaw clamped position; a jaw nominal position to a jaw spread position; or a jaw clamped position to a jaw spread position. The angles may be about 5 degrees or more, about 10 degrees or more, about 15 degrees or more, about 30 degrees or more, about 45 degrees or more, or about 60 degrees or more. The angles may be about 180 degrees or less, about 160 degrees or less, about 135 degrees or less, about 105 degrees or less, or about 90 degrees or less. The clamp lever when moved towards the fixed handle (e.g., moved proximally or towards the jaw clamped position) may distally axially move the forceps toward an end of the surgical device, close the forceps, cause gripping of the forceps, or a combination thereof. The clamp lever when moved in a way clamped position may be located proximate to or in contact with the fixed handle.

The clamp lever clamped position may be a position where the clamp lever functions to clamp the forceps. The clamp lever when moved proximally, towards the jaw clamped position, may cause the forceps to extend out of the stylet, outer tube, inner tube, or a combination thereof; close the jaws; move the jaw arm, or a combination thereof. The clamp lever when moved proximally, towards the jaw clamped position, may cause the forceps to move proximally, a portion to extend into the stylet, or both so that the jaws of the forceps are closed or create a gripping force. When the clamp lever is in the clamp lever clamped position, the forceps may be in the jaw clamped position and the jaws may grip a feature of interest, an anatomical feature, or a combination thereof. The clamp lever clamped position may cause the forceps to clamp. The clamp lever in the clamp lever clamped position may have a force imparted upon the clamp lever. The clamp lever clamped position may have a force created thereupon (e.g., either directly or indirectly) by the return bias member. The clamp lever clamped position may have the clamp lever being free of a force (e.g., directly or indirectly) by the stop bias member. The clamp lever clamped position may be formed by moving the clamp lever in a first direction. The clamp lever clamped position may be formed by moving the clamp lever towards the stop bias member, towards the return bias member, away from the stop bias member, away from the return bias member, the movement actuator deflecting or deforming the return bias member, the movement actuator deflecting or deforming the stop bias member, or a combination thereof. The clamp lever may include one or more surfaces. Preferably, the clamp lever has a plurality of surfaces. For example, the clamp lever may have a first surface for moving the clamp lever proximally to clamp the jaws and a second surface for moving the clamp lever distally to spread the jaws. The clamp lever in the clamp lever clamped position may move in a first direction and the clamp lever may move in a second opposing direction to the clamp lever spread position.

The clamp lever spread position may be a position where the clamp lever functions to separate the jaws of the forceps beyond a jaw nominal position. The clamp lever spread position may be a position where the clamp lever is moved closer to the fixed handle than the clamp lever in the clamp lever clamped position. The clamp lever spread position may be a position where the clamp lever is moved farther from the fixed handle than when the clamp lever is in the jaw clamped position, the jaw nominal position, or both. The clamp lever spread position may be a position where the clamp lever is moved away from the fixed handle. The clamp lever spread position may move the jaws apart. The clamp lever spread position may move the jaws apart so that one or both jaws may be used for blunt dissection. In blunt dissection, the end effector or bodies may be placed into an area, such as an intended dissection plane, while in the closed position and then moved into an open position. Moving the end effector or bodies into the open position may cause the top surface, the bottom surface, the side surfaces, the front surfaces, or a combination thereof to spread, move, and/or reposition a vessel or tissue. The clamp lever, the movement actuator, or both may pivot about a grounding member when the clamp lever, the movement actuator are moved.

The one or more grounding members function to connect all or a portion of one or more movable components (e.g., a trigger, clamp lever, four bar mechanism, movement actuator, operable mechanism) of the surgical device to a fixed portion of the surgical device so that one or both ends of the movable component may be prevented from translating, the movable component may move rotationally, or both. The one or more grounding members may be part of the handle. The one or more grounding members may be part of the housing. The one or more grounding members may be part of the handpiece. The one or more grounding members may be part of the stylet. The one or more grounding members may be part of the fixed handle. Preferably, the housing includes one or more molded portions that connect to one or more movable components. More preferably, the one or more grounding members may connect to a trigger, clamp lever, movement actuator, actuator, four bar mechanism, operable mechanism, or a combination thereof. The one or more grounding members may connect to an end region or an end of a component (e.g., an end region of a trigger, clamp lever, movement actuator) so that an opposing end may be movable. The grounding member may prevent movement of all or a portion of a component taught herein and an return bias mechanism, stop bias mechanism, or both may impart movement into a movable portion of the component (e.g., trigger, clamp lever, four bar mechanism, operable mechanism, movement actuator, actuator, or a combination thereof).

The return bias member may function to return all or a portion of a surgical device to a nominal position (e.g., trigger, jaw, forceps, clamp lever, stylet, blade). The device may include one or more return bias members. The surgical device may include a plurality of return bias members. Preferably, each component of the surgical device when in contact with a return bias member is only in contact with a single return bias member. The return bias member may move or clamp lever away from a fixed handle. The return bias member may move forceps from a clamped position, a spread position, or both to a nominal position. The return bias member may assist in actuating one or more assemblies. The return bias member may return the one or more assemblies to a neutral position and/or a resting position after actuation. The return bias member may be any device that biases the tubular member and/or stylet to a resting position so that when the tubular member and/or stylet is actuated and released from actuation the tubular member and/or stylet returns back to a resting position. The return bias member may actuate a four bar mechanism, an operable mechanism, a forceps, a blade, a stylet, a movement actuator, an actuator, or a combination thereof either directly or indirectly. The return bias member may be and/or include a biasing member (e.g., a spring structure, an elastic member, a compressible member, a stretchable member, rubber, a rubber grommet, any structure that can be compressed and released, or a combination thereof). The return bias member may be a return spring. The return bias member when the device is in a nominal position may be free of any load. The return bias member when the device is in a nominal position may be pre-loaded. For example, the return bias member may impart some load upon the actuator, movement actuator, trigger, clamp lever, or a combination thereof even when the device is in the nominal position. In the nominal position, any pre-load on the return bias member may be matched by a preload on the stop bias member. The return bias member may apply a force or a pre-load of about 0.5 N or more, about 1 N or more, about 1.5 N or more, or about 2 N or more. The return bias member may apply a force or pre-load of about 10 N or less, about 7 N or less, or about 5 N or less. The return mechanism may be connected to a proximal end of a stylet, a tubular member, a blade, forceps, a blade shaft, forceps shafts, stylet, or a combination thereof. A proximal end of the tubular member may be disposed in the cavity of the hand piece and one or more functional assemblies (e.g., a gripping assembly, a cutting assembly, or both) may be located at a distal end of the stylet, tubular member, or both. The return bias member may be located on a distal side of an actuator, a movement actuator, or both. The return bias member may be located between a collar on a stylet, forceps, blade, or a combination thereof and a movement actuator. The return bias member may be compressed, deformed, deflected, or a combination thereof when the trigger, clamp lever, or both are moved towards the jaw clamped position, the fixed handle, or both. The return bias member may move the clamp lever towards a nominal position. The return bias member may be located opposite a stop bias member.

The stop bias member may function to stop clamp lever, actuator, movement actuator, or a combination thereof in their respective nominal positions; oppose a return bias member force; or both. The stop bias member may stop the actuator, movement actuator, clamp lever, or a combination thereof at a nominal position. The stop bias member may provide a force that opposes a force of the return bias member. The stop bias member may be compressible, deformable, deflectable, or a combination thereof. The stop bias member in its nominal position may be have a pre-load, no load, have a positive pre-load, a negative pre-load, or a combination thereof. The bias stop member may be located on a proximal side of the movement actuator. The bias stop member may be made of the same material as the return bias member. The bias stop member may be a spring structure, an elastic member, a compressible member, a stretchable member, rubber, a rubber grommet, any structure that can be compressed and released, or a combination thereof. The bias stop member preferably is a spring. The bias stop member may apply a force or a pre-load of about 0.5 N or more, about 1 N or more, about 1.5 N or more, or about 2 N or more. The bias stop member may apply a force or pre-load of about 10 N or less, about 7 N or less, or about 5 N or less. A force or pre-load of the bias stop member may equal a force or pre-load of the return bias member when both are in a nominal position. The bias stop member may be movable or compressible so that the trigger or clamp lever may be over rotated to allow the jaws, forceps, or both to spread upon an application of force that overcomes the force of the bias stop member, the pre-load, or both. The stop bias member may be fixed within a surgical device. One side of a stop bias member may be movable and one side of a stop bias member may be fixed or in contact with an immovable member. For example, the stop bias member may be located between a portion of the housing, that prevents movement of the stop bias member, and the movement actuator, which may move a portion of the stop bias member. The stop bias member may be one or more bias stop members. The bias stop member may be a plurality of bias stop members. For example, the bias stop member may be two springs that are concentric and the first spring may provide a first amount of force or resistance and a second spring may provide a greater amount of resistance. Each bias stop member may increase in resistance as the trigger, clamp lever, or both are moved axially relative to the bias stop member (e.g., in a proximal direction). The one or more stop bias members may impart a force upon a movement actuator. The one or more stop bias members may deflect, compress, deform, or a combination thereof to stop the movement actuator (and attached components such as a clamp lever and forceps) at a nominal position.

The movement actuator may function to axially move the forceps, blade, stylet, or a combination thereof. The movement actuator may function to close the forceps, open the forceps, or both. The movement actuator may be directly connected to the trigger, the clamp lever, or both. The movement actuator may be indirectly connected to the trigger, clamp lever, or both. The movement actuator may be part of an operable mechanism or four bar mechanism as taught herein. The movement actuator may move along an arc. The movement actuator may have one fixed end or fixed end region and one movable end or movable end region. The movable end may be moved by a trigger or clamp lever, a link that connects the trigger or clamp lever to the movement actuator, or a combination thereof. The fixed end or fixed end region may be connected to a grounding member of the surgical device, handpiece, housing, or a combination thereof.

The grounding member may function to prevent axial or longitudinal movement of a movement actuator but permit rotational movement. The grounding member may connect an end or end region of a movement actuator to a housing or handpiece so that a portion of grounding member is fixed (e.g., laterally, longitudinally, axially) relative to the handpiece, housing, or both. The grounding member may act as a bearing surface. The grounding member may allow for or assist in rotational movement of the movement actuator so that the movement actuator axially moves the forceps, blade, stylet, or a combination thereof. The grounding member may be portion of the housing that extends orthogonal to the housing. The grounding member may extend into a portion of the movement actuator. The grounding member may hold one end or end region of a movement actuator so that the movement actuator when moved, moves the forceps, stylet, blade, or a combination thereof.

The forceps may function to grip, hold, move, adjust, pull, remove, or a combination thereof an anatomical feature, tissue, a feature of interest, or a combination thereof. The forceps may include one or more jaws and the jaws may rotate about a hinge. The forceps may include a ramp or bump that when the forceps are axially moved towards the outer tube or stylet the forceps are compressed to create a gripping force. The stylet or outer tube may over run the forceps to close the forceps. The jaws may be free of a ramp or bump. Preferably, the forceps are rigid body jaws that are rotated about a pivot by a jaw arm. Preferably, the jaws are longitudinally static and rotationally move by a force generated by a jaw arm. The forceps may be connected to an end of the stylet. The forceps may have a portion that is connected to an end of a stylet and a portion that extends through the stylet. The forceps may include serrations, be smooth, have teeth, or a combination hereof. The forceps may include a groove that a blade extends through to cut an anatomical feature, tissue, a feature of interest, or a combination thereof held between the forceps. The forceps may have fixed ends at the stylet and may rotate about the fixed ends. The forceps may move laterally towards and away from each other within a single plane. The forceps may rotate about an axis. The forceps may be connected to the stylet.

The stylet as discussed herein may include a tubular member or may be the tubular member. The stylet may include a tubular member (e.g., an outer tube) and an inner shaft, or inner tube. The stylet may include a tubular member that extends around all or a portion of an inner tube. The tubular member may function to extend into a patient during a surgical procedure so that a user (i.e., surgeon) can perform one or more surgical procedures. The tubular member may be flexible so that the tubular member may be moved within a patient. Preferably, the tubular member may be substantially rigid so that the tubular member may be moved to a desired location. The tubular member includes a distal end and a proximal end. The distal end may be an end of the tubular member that is located farthest from the hand piece (e.g., the end of the tubular member that is inserted into a patient). The proximal end of the tubular member may be the end of the tubular member located proximate to the user, in the hand piece, or both. For example, the proximal end may extend into the handpiece so that manipulation of the one or more operable mechanisms manipulates the tubular member. The tubular member and its components may be made of any biocompatible material, for example, stainless steel, plastic, a synthetic material, a natural material, or a combination thereof. The tubular member may comprise a tubular member sub-assembly. The tubular member sub-assembly may include one or more hollow tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, or a combination thereof.

The one or more outer tubes may function to close the jaws, anchor the jaws, support the jaws, or a combination thereof. The one or more tubes may function to protect the inner tube. The one or more jaws may move relative to the inner tube, the outer tube, or both (e.g., pivot about). The one or more jaws may axially move towards the distal end and the proximal end during movement of the outer tube. The one or more outer tubes, jaws, or both may be axially static. The one or more outer tubes may connect the jaws together, connect to the jaws individually, assist in closing the jaws, support the jaws, or a combination thereof. The one or more outer tubes may house one or more shafts (e.g., jaw arm) that extend into contact with the jaws to open and close the jaws. The one or more tubes may support the jaws in a cantilever position. The one or more jaw arms may extend through the outer tube, an inner tube, or both.

The one or more inner tubes may function to create a point of contact for one or more jaws. The one or more inner tubes may function to connect to a shaft (e.g., camming shaft). The one or more inner tubes may function to extend through all or a portion of the outer tube. The one or more inner tubes may form a connection point, include a connection feature (e.g., a pin, bolt, screw, rivet, or a combination thereof) for one or more jaws. The connection feature may be a pivot that the jaws rotate about relative to the one or more inner tubes. The one or more inner tubes may connect to a pivot joint of one or more jaws so that the one or more jaws rotate about an axis. The one or more inner tubes may assist in opening and closing the jaws. The one or more inner tubes may be movable relative to an outer tube. The one or more inner tubes may be static and an outer tube may be movable relative to the inner tube. Both an inner tube and an outer tube may be axially static. The one or more inner tubes may be substantially the same length as an outer tube. The one or more inner tubes may be shorter than an outer tube. The one or more inner tubes may be in communication with a shaft (e.g., a shaft connected to each of the jaws, the blade, or both). The stylet may be free of an inner tube. The one or more inner tubes may be located between a tubular member and a hollow tube.

The two or more opposing jaws may function to create a gripping force. Two jaws when connected together may form forceps. The two or more opposing jaws may move towards each other to create a gripping force, to grip a feature of interest, or both. The two or more opposing jaws may be any devices that may be used to grip items of interest in surgery, for example laparoscopic surgery. The two or more opposing jaws may function to be used to grip or clamp an item of interest, an anatomical feature, tissue, or a combination thereof for cutting or electrical therapy (e.g., coagulation, cauterizing, electrically cutting). The two or more opposing jaws may be any shape and size so that the jaws perform a gripping function, create a gripping force, or both. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The two opposing jaws may include a gap (e.g., a blade track) to allow for a cutting instrument to be inserted while retaining functionality of the two or more opposing jaws.

The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. Preferably, the jaws are made of a biocompatible material. More preferably, the jaws are made of a material that conducts electricity. The two opposing jaws may be made of a material that conducts electricity. The jaws may include a protective cover.

The two opposing jaws may be used to apply electricity to a feature of interest that may be gripped by the two opposing jaws. The gripping portion of the two opposing jaws may have a surface texture to grip a feature of interest. For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be biased from an open position to a closed position by retraction of one of the one or more jaw shafts, movement of the one or more tubular members towards the distal end, or both along an axis of the one or more tubular members. The two opposing jaws may include a jaw bias mechanism (e.g., a return bias member and/or a stop bias member), be part of a jaw bias mechanism, or both. The two opposing jaws may have laterally extending arcuate sections at the proximal end (e.g., heel of the jaw) of the jaws that protrude out from the distal end of the tubular member. The jaws may be used for dissection. The jaws may be a probe. The jaws may be spread apart to move tissue, an anatomical feature, a feature of interest, or a combination thereof. The jaws may be connected together by one or more jaw arms.

The jaw arms may function to open, close, rotate, actuate, spread, or a combination thereof the jaws. The jaw arms may be connected to a single jaw. The jaw arms may be connected to both jaws or all of the jaws. The jaw arms may be in communication with the clamp lever so that when the clamp lever is moved the jaws are moved. The jaw arms may extend through the stylet or be part of the stylet. The jaw arms may be directly connected to the jaws, the clamp lever, or both. The jaw arms may be indirectly connected to the jaws, the clamp lever, or both. For example, the jaw arms may be connected to an operable mechanism that is connected to the clamp lever. The jaw arms may be moved axially to move the jaws. The jaw arms may reciprocate. The jaws may be moved between a jaw nominal position, jaw clamped position, jaw spread position, or a combination thereof by the jaw arms.

The jaw nominal position may be a position where the jaws stop when no external forces are applied to the jaws. The jaw nominal position may have the jaws separated by a distance. The jaw nominal position may have the jaws open. The jaw nominal position may have the jaws separated by a distance that is sufficiently large that a vein, artery, tissue, cyst, anatomical feature, feature of interest, or a combination thereof may fit between the jaws. The jaw nominal position may be where the movement actuator is at rest. The jaw nominal position may be where the forces of the return bias member and the stop bias member are equalized. In the jaw nominal position the jaws may be separated by a distance of about 10 cm or less, about 7 cm or less, or about 5 cm or less. In the jaw nominal position the jaws may be separated by about 5 mm or more, about 1 cm or more, or about 2 cm or more. The jaw nominal position may be when the jaws are between a jaw clamped position and a jaw spread position.

The jaw clamped position may be a position where the jaws are in contact; a vein, artery, tissue, cyst, anatomical feature, feature of interest, or a combination thereof is between the jaws; the clamp lever is moved towards the fixed handle; or a combination thereof. The jaw clamped position may be any position where the jaws are moved towards each other from the jaw nominal position. The jaw clamped position may be where the jaws are moved towards each other and a feature is held between the jaws and the jaws are restricted from closing further. The jaw clamped position may have a distance between the jaws of about 2 cm or less, about 1 cm or less, 5 mm or less, 1 mm or less, or the jaws are in contact.

The jaw spread position may be a position where the jaws are spaced apart a distance greater than a position where the jaws are in the jaw nominal position. The jaw spread position may be where a force is exerted upon the jaws in a direction opposing the jaw clamped position. The jaw spread position may be where the jaws are spread so that the jaws may be used for dissection, movement, or both of an anatomical feature or a feature of interest. The jaw spread position may be where the jaws are located a distance apart that is of the jaw nominal position plus about 1 mm or more, about 3 mm or more, about 5 mm or more, about 7 mm or more, or about 1 cm or more. The jaw spread position may be the jaws located the jaws clamped position apart plus about 10 cm or less, about 7 cm or less, about 5 cm apart or less, or about 3 cm apart or less.

FIG. 1A is a side view of a surgical device 2 (which is an electrosurgical device as shown). The surgical device 2 includes a handpiece 16 connected to a stylet 40. The handpiece 16 includes a fixed handle 4 proximate to a trigger 6 and a clamp lever 8 that are each individually movable relative to the fixed handle 4. The trigger 6 and the clamp lever 8 extend from the housing 10 and are connected to the surgical device 2 within the housing 10. The stylet 40 extends from the housing 10 in a distal direction. The stylet 40 includes an outer tube 42 having forceps 14 that extend from the outer tube 42. The forceps 14 include a pair of jaws 60 that are resilient.

Figure 1B:
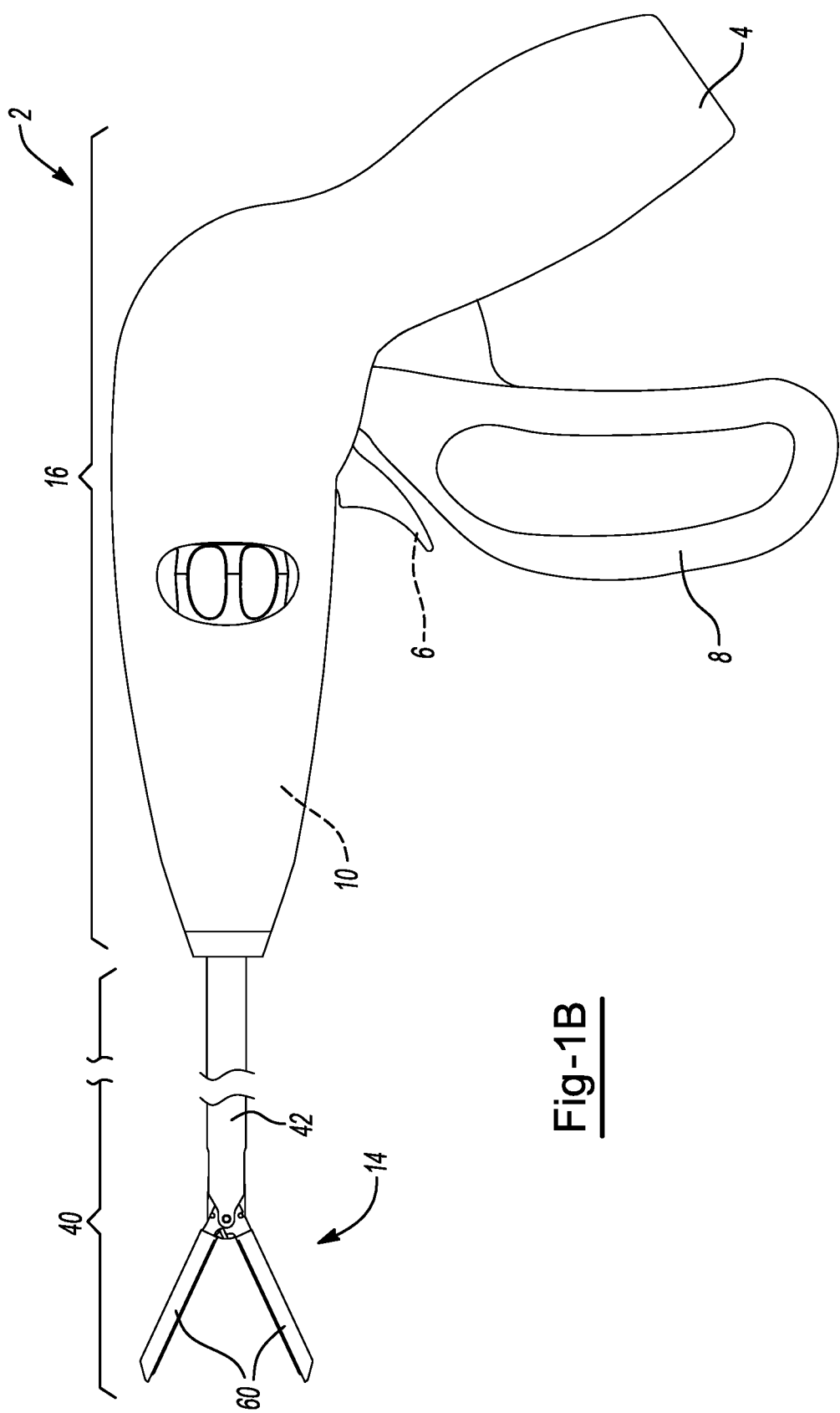
FIG. 1B illustrates a side view of laparoscopic forceps with rigid body jaws

FIG. 1B is a side view of a surgical device 2. The surgical device 2 includes a handpiece 16 connected to a stylet 40. The handpiece 16 includes a fixed handle 4 proximate to a trigger 6 and a clamp lever 8 that are each individually movable relative to the fixed handle 4 with the trigger 6 and clamp lever 8 being connected to the handpiece 16 by a housing 10. A stylet 40 extends from the housing 10 in a distal direction and includes an outer tube 42. The jaws 60 of the forceps 14 extend out of the outer tube 42, with the jaws 60 being rigid body jaws 60.

Figure 2A:
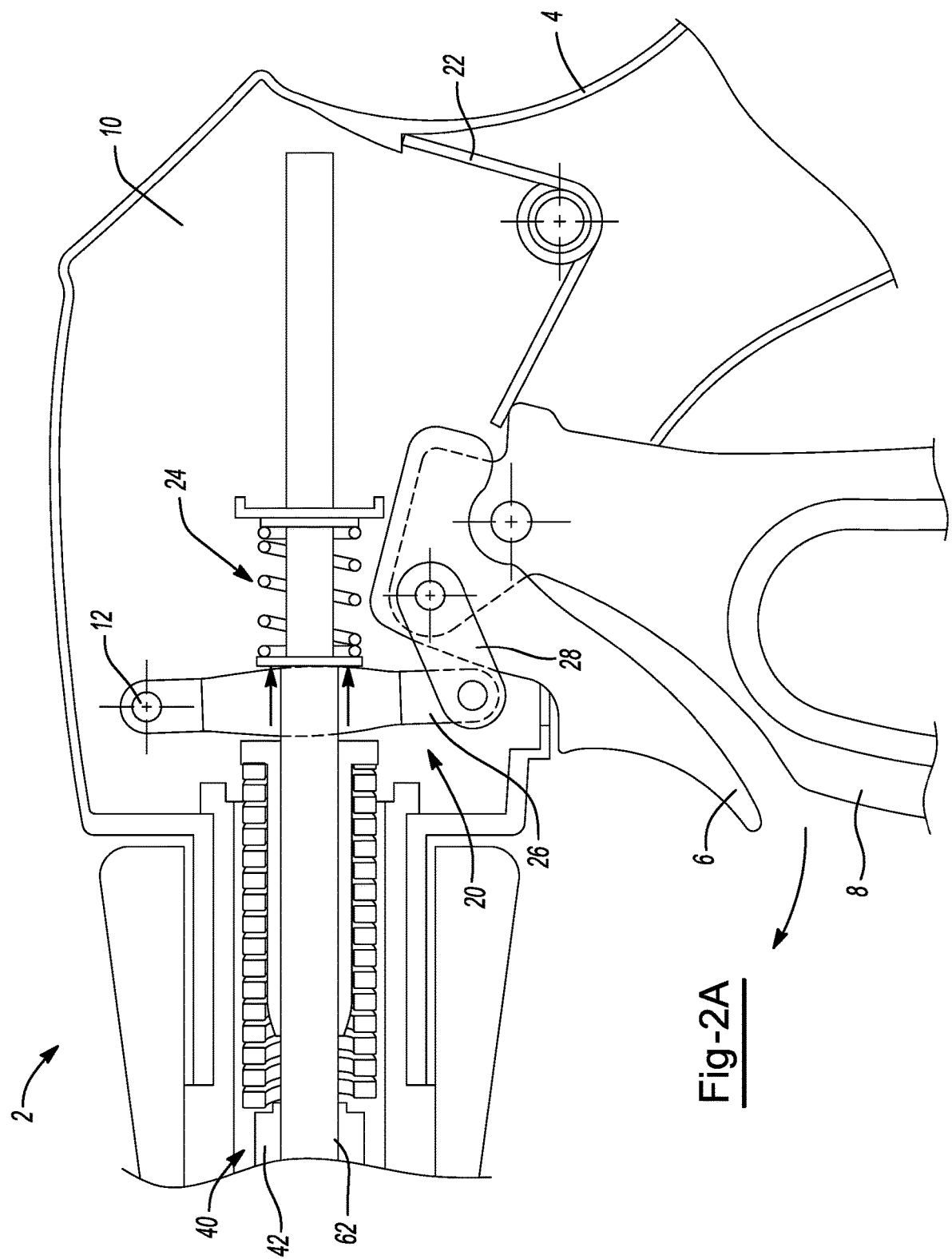
FIG. 2A illustrates a partial cross-sectional view of the housing of the forceps of FIG. 1A when the jaws are in the jaw nominal position.

FIG. 2A is a partial cross-sectional view of a surgical device 2 of FIG. 1A cut along lines II-II. The surgical device 2 includes a housing 10 with a fixed handle 4, a trigger 6, and clamp lever 8. The clamp lever 8 is connected to an actuator 20 and the housing 10. The actuator 20 is coupled to a jaw arm 62 and is located between a return bias member 22 and a stop bias member 24 so that when the clamp lever 8 is moved in a first direction the jaw arm 62 compresses the return bias member 22 moving the jaw arm 62 in a first direction and when the clamp lever 8 is moved in a second direction the stop bias member 24 is compressed and the jaw arm 62 is moved in a second direction. The actuator 20 includes a movement actuator 26 that is connected to the housing 10 by a grounding member 12 at an end opposite of end that is in communication with the clamp lever 8. The stylet 40 includes a jaw arm 62 located within an outer tube 42.

Figure 2B:
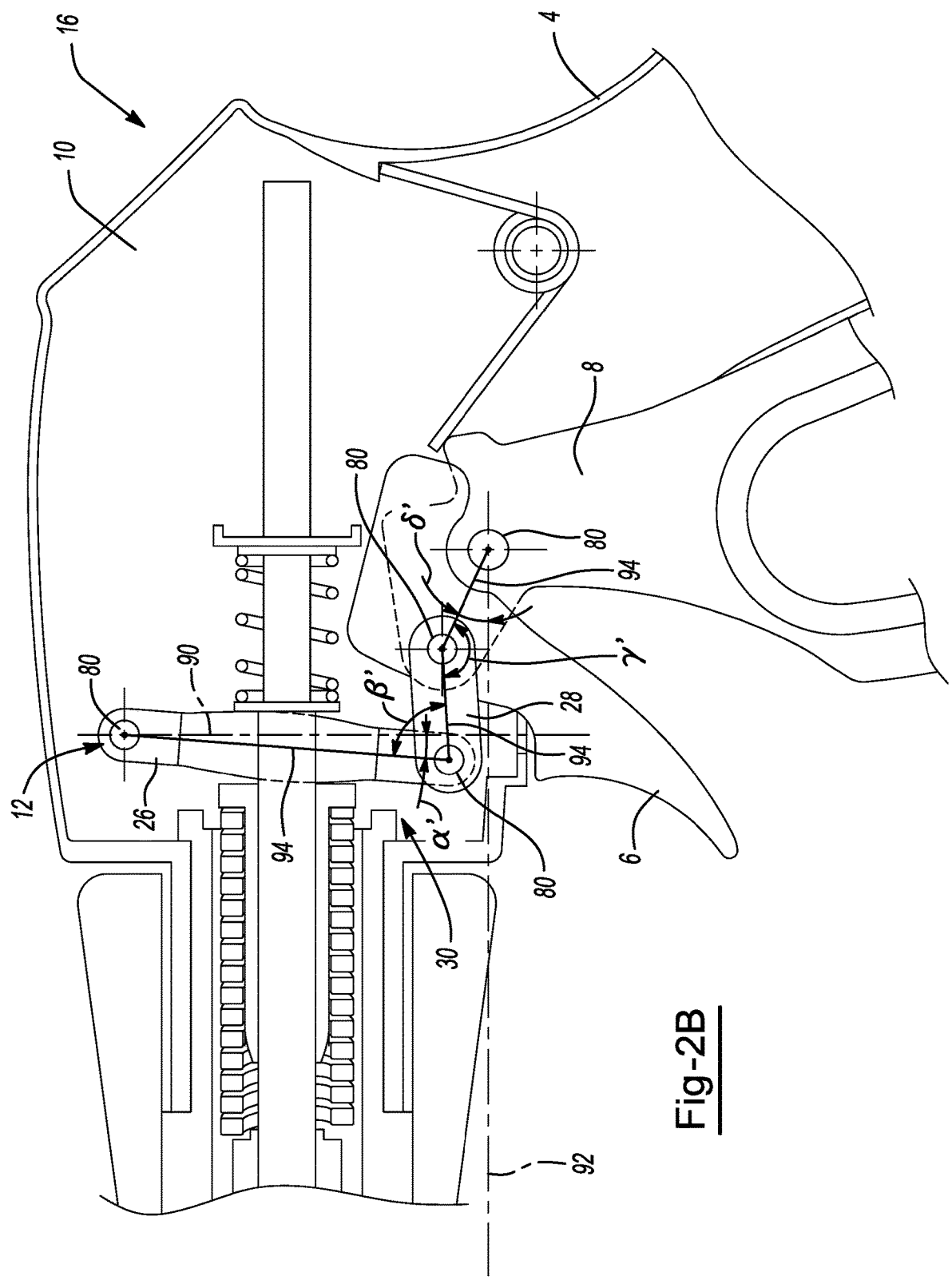
FIG. 2B illustrates a partial cross-sectional view of the housing of the forceps when the jaws are in the jaw clamped position.

FIG. 2B illustrates an operable mechanism 30 located within the handpiece 16. The handpiece 16 includes a housing 10 that forms a portion of the operable mechanism 30. The operable mechanism 30 is an actuator 20 that includes a movement actuator 26 and a coupler 28 connected to the clamp lever 8. The movement actuator 26, coupler 28, and clamp lever 8 each include a rotational axis 80 that each respective member pivots around when moved between positions. The rotational axis 80 of the movement actuator 26 is a grounding member 12. As shown, the movement actuator 26 is moved and angled ($\alpha'$) relative to the vertical nominal axis 90 to a clamped axis 94. The coupler 28 is moved so that an angle ($\beta'$) is located between the clamped axis 94 of the movement actuator 26 and the coupler 28. The clamp lever 8 is moved so that a clamped axis 94 of the clamp lever 8 is located at an angle ($\gamma'$) from the clamped axis of the coupler. The clamp lever 8 in the clamped position is located an angle ($\delta'$) from the horizontal nominal axis 92 and the clamp lever 8 moves away from the trigger 6 and towards the fixed handle 4.

Figure 2C:
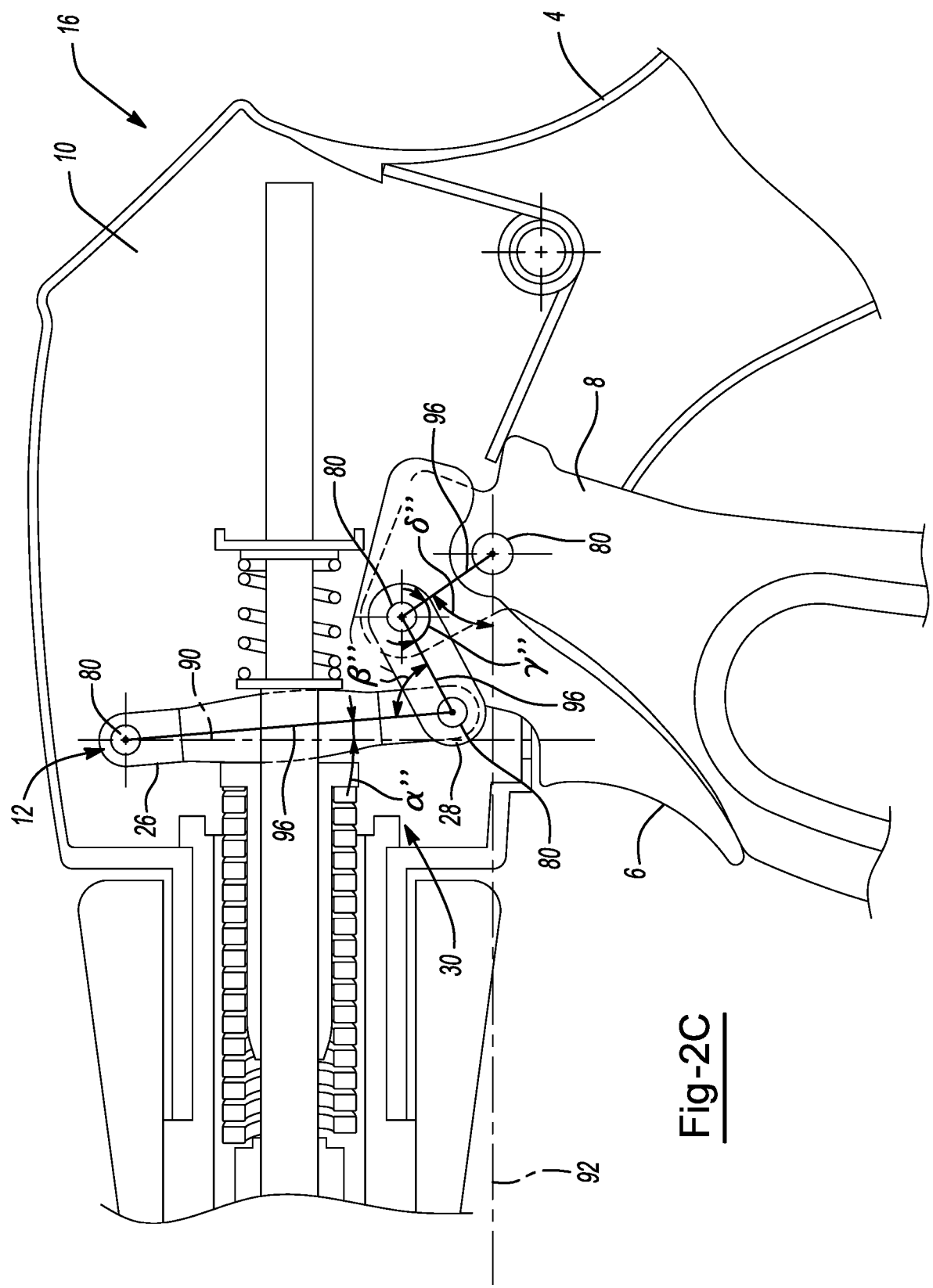
FIG. 2C illustrates a partial cross-sectional view of the housing of the forceps when the jaws are in the jaw spread position.

FIG. 2C illustrates an operable mechanism 30 located within the handpiece 16 when the jaws (not shown) are moved to the jaw spread position. The handpiece 16 includes a housing 10 that forms a portion of the operable mechanism 30. The operable mechanism 30 is an actuator 20 that includes a movement actuator 26 and a coupler 28 connected to the clamp lever 8. The movement actuator 26, coupler 28, and clamp lever 8 each include a rotational axis 80 that each respective member pivots around when moved between positions. The rotational axis 80 of the movement actuator 26 is a grounding member 12. As shown, the movement actuator 26 is moved and angled ($\alpha''$) relative to the vertical nominal axis 90 to a spread axis 96. The coupler 28 is moved so that an angle ($\beta''$) is located between the spread axis 96 of the movement actuator 26 and the coupler 28. The clamp lever 8 is moved so that a spread axis 96 of the clamp lever 8 is located at an angle ($\gamma''$) from the clamped axis of the coupler. The clamp lever 8 in the spread position is located an angle ($\delta''$) from the horizontal nominal axis 92 and the clamp lever 8 moves towards the trigger 6 and away from the fixed handle 4.

Figure 3A:
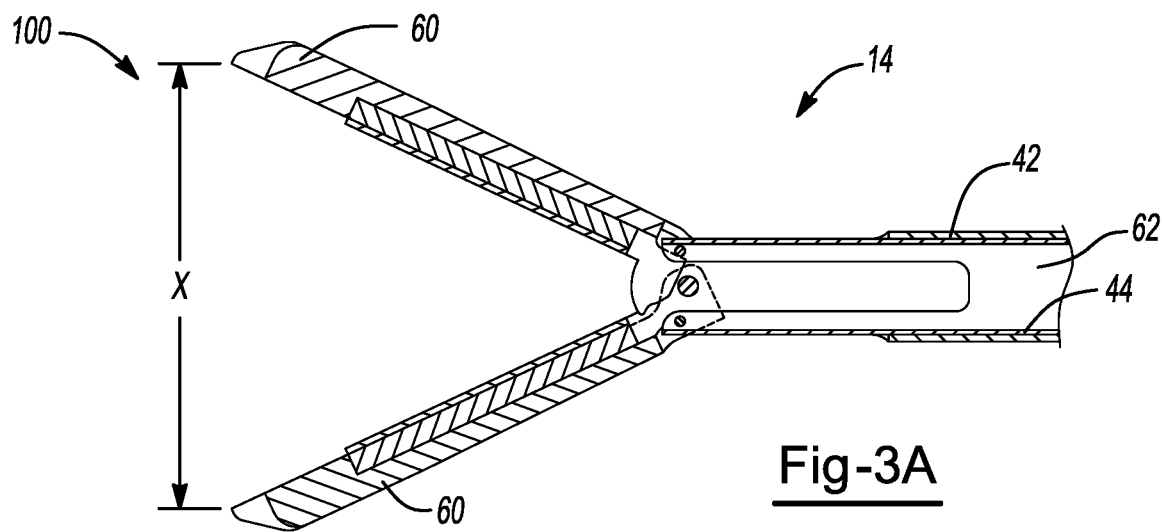
FIG. 3A is a cross-sectional view of a stylet and jaws with the jaws of the forceps in a jaw nominal position.

FIG. 3A illustrates a cross-sectional side view of jaws 60 of the forceps 14 extending from an outer tube 42. The jaws 60 are in the jaw nominal position 100 where the jaws 60 are separated by a distance (X). The jaws 60 are connected to the clamp lever (not shown) by jaw arm 62 that extends through the inner tube 44 and the outer tube 42. The jaw arm 62 actuates both jaws 60 when the clamp lever (not shown) is moved.

Figure 3B:
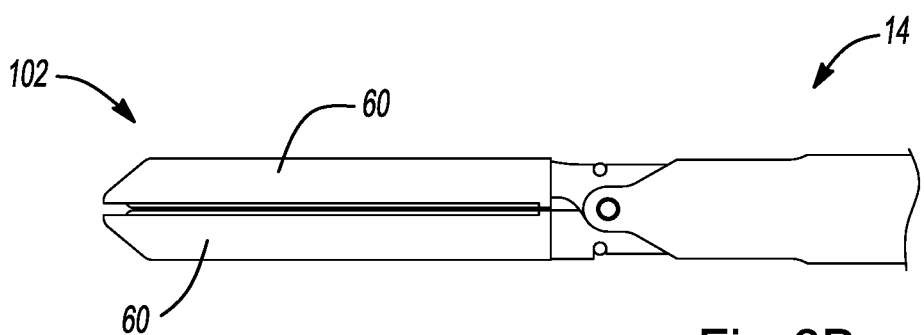
FIG. 3B is a side view of the jaws of the forceps in a jaw clamped position.

FIG. 3B illustrates a side view of the jaws 60 of the forceps 14 being in a jaw clamped position 102.

Figure 3C:
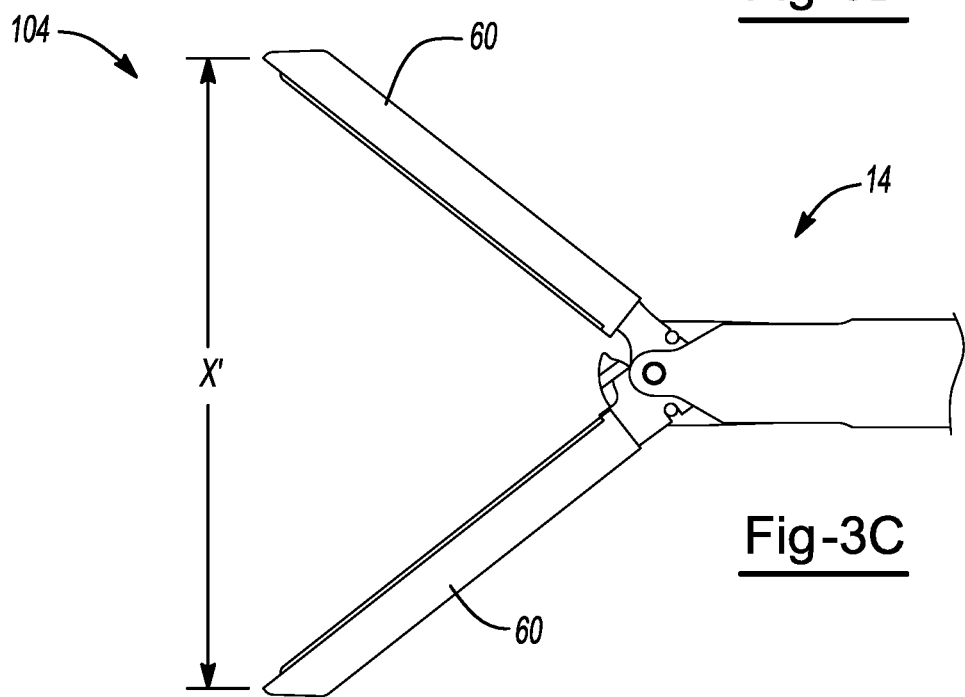
FIG. 3C is a side view of the jaws of the forceps in a jaw spread position.

FIG. 3C is a side view of the jaws 60 of the forceps 14 in a jaw spread position 104 where the jaws 60 are opened a distance (X') which is greater than the distance (X) of the jaw nominal position as is illustrated in FIG. 3A.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Surgical device
4 Fixed handle
6 Trigger
8 Clamp lever
10 Housing
12 Grounding member
14 Forceps
16 handpiece
20 Actuator
22 return bias member
24 Stop bias member
26 Movement Actuator
28 Coupler
30 Operable mechanism
40 Stylet
42 Outer tube
44 Inner tube
60 Jaws
62 Jaw arm
80 Rotational axis
90 Vertical Nominal axis
92 Horizontal nominal axis
94 Clamped axis
96 Spread axis
100 Jaw Nominal position
102 Jaw Clamped position
104 Jaw spread position

We claim:

1. A surgical device comprising:
a handpiece;
a forceps attached to the handpiece, the forceps including:
   a first jaw; and
   a second jaw opposing the first jaw, wherein the first jaw and the second jaw are movable relative to one another between a jaw nominal position and a jaw clamped position;
a clamp lever extending from the handpiece and in communication with the first jaw and the second jaw, wherein the clamp lever is operable to move the first jaw and the second jaw from the jaw nominal position to the jaw clamped position when an external force is imparted upon the clamp lever in a first direction;
a stop bias member that stops movement of the clamp lever when the external force is removed so that the first jaw and the second jaw are in the jaw nominal position at rest; and
a return bias member;
wherein the first jaw and the second jaw are movable from the jaw nominal position to a jaw spread position when the clamp lever is moved in a second direction that opposes the first direction by an external force deforming the stop bias member so that a distance between the first jaw and the second jaw is larger in the jaw spread position than in the jaw nominal position; and
wherein the return bias member provides a force in a first direction and the stop bias member provides a force in a second direction that opposes the return bias member force so that a net force is zero.

2. The surgical device of claim 1, wherein the stop bias member is a compression spring.

3. The surgical device of claim 2, wherein the compression spring has a pre-load.

4. The surgical device of claim 2, wherein the compression spring has a natural length and the compression spring is at the natural length when the compression spring is free of contact with the clamp lever.

5. The surgical device of claim 1, wherein the surgical device includes a fixed handle extending from the handpiece and the clamp lever is movable relative to the fixed handle in the first direction and the second direction.

6. The surgical device of claim 5, wherein the surgical device includes a trigger extending from the handpiece, and wherein the clamp lever is disposed between the fixed handle and the trigger.

7. The surgical device of claim 1, wherein the clamp lever is in communication with one or more inner tubes that are connected to the first jaw and the second jaw.

8. The surgical device of claim 7, wherein the one or more inner tubes are a push rod that pushes the first jaw and the second jaw in a first direction so that the first jaw and the second jaw move from the jaw nominal position to the jaw clamped position and so that the first jaw and the second jaw move from the jaw nominal position to the jaw spread position.

9. The surgical device of claim 1, wherein the clamp lever is connected to one or more actuators.

10. The surgical device of claim 9, wherein the one or more actuators are connected to one or more inner tubes and movement of the one or more actuators moves the one or more inner tubes and the first jaw and the second jaw.

11. The surgical device of claim 9, wherein at least one of the one or more actuators are located between the return bias member and the stop bias member.

12. The surgical device of claim 9, wherein the one or more actuators includes a movement actuator that has a first portion that is connected to a housing of the surgical device at a grounding member and a second end opposite the first portion that is in communication with and moved by the clamp lever.

13. The surgical device of claim 12, wherein the movement actuator is directly connected to the clamp lever.

14. The surgical device of claim 12, wherein the movement actuator is indirectly connected to the clamp lever.

15. A surgical device comprising:
a handpiece;
a forceps attached to the handpiece, the forceps including;
   a first jaw; and
   a second jaw opposing the first jaw, wherein the first jaw and the second jaw are movable relative to one another between a jaw nominal position and a jaw clamped position;
a clamp lever extending from the handpiece and in communication with the first jaw and the second jaw, wherein the clamp lever is operable to move the first jaw and the second jaw from the jaw nominal position to the jaw clamped position when an external force is imparted upon the clamp lever in a first direction;
a stop bias member that stops movement of the clamp lever when the external force is removed so that the first jaw and the second jaw are in the jaw nominal position at rest; and a return bias member that biases the clamp lever back against the stop bias member moving the clamp lever into the jaw nominal position;

wherein the first jaw and the second jaw are movable from the jaw nominal position to a jaw spread position when the clamp lever is moved in a second direction that opposes the first direction by an external force deforming the stop bias member so that a distance between the first jaw and the second jaw is larger in the jaw spread position than in the jaw nominal position.

16. The surgical device of claim 15, wherein the stop bias member is pre-loaded so that when the return bias member moves to the jaw nominal position, the stop bias member is free of further compression.

17. The surgical device of claim 16, wherein when the external force is applied in the second direction the stop bias member is further deformed and the first jaw and the second jaw are moved to the jaw spread position.

18. A surgical device comprising:

a handpiece;

a first jaw;

a second jaw opposing the first jaw, wherein the first jaw and the second jaw are movable relative to one another between a jaw nominal position and a jaw clamped position;

a fixed handle extending from the handpiece;

a trigger extending from the handpiece;

a movable clamp lever extending from the handpiece and disposed between the fixed handle and the trigger, the clamp lever in communication with the first jaw and the second jaw, wherein the clamp lever is operable to move the first jaw and the second jaw from the jaw nominal position to the jaw clamped position when an external force is imparted upon the clamp lever in a first direction; and a stop bias member that stops movement of the clamp lever when the external force is removed so that the first jaw and the second jaw are in the jaw nominal position at rest;

wherein the first jaw and the second jaw are movable from the jaw nominal position to a jaw spread position when the clamp lever is moved in a second direction that opposes the first direction by an external force deforming the stop bias member so that a distance between the first jaw and the second jaw is larger in the jaw spread position than in the jaw nominal position.

* * * * *